United States Patent
Caralt Batlle

[11] Patent Number: 5,114,410
[45] Date of Patent: May 19, 1992

[54] DISPOSABLE HYPODERMIC SYRINGE

[76] Inventor: Jaime Caralt Batlle, Barri del Pi, 15, 08230 Matapedrera, Barcelona, Spain

[21] Appl. No.: 642,303

[22] Filed: Jan. 18, 1991

[51] Int. Cl.$^5$ .............................................. A61M 5/00
[52] U.S. Cl. ................................... 604/195; 604/198; 604/110
[58] Field of Search ............... 604/195, 198, 192, 187, 604/263, 110, 218, 220

[56] References Cited

U.S. PATENT DOCUMENTS

| | | | |
|---|---|---|---|
| 4,838,869 | 6/1989 | Allard | 604/195 |
| 4,874,382 | 10/1989 | Lindemann et al. | 604/195 |
| 4,921,486 | 5/1990 | DeChellis et al. | 604/195 X |
| 4,927,414 | 5/1990 | Kulli | 604/110 |
| 4,946,446 | 8/1990 | Vadher | 604/198 |
| 4,955,870 | 9/1990 | Ridderheim et al. | 604/195 |
| 4,978,343 | 12/1990 | Dysarz et al. | 604/195 |

*Primary Examiner*—John D. Yasko
*Attorney, Agent, or Firm*—Cushman, Darby & Cushman

[57] ABSTRACT

A disposable hypodermic syringe, comprising a tube, with its front part narrowed and adapted to receive a hypodermic needle, and a hollow piston capable of sliding through the inside of the tube; obturating devices laid across and held in operative position by the head of the needle; a spring, that tends to push the needle towards the inside of the tube; a closing device of the piston's cavity; and irreversible joining devices to fit other complementary joining devices placed at the head of the needle. The obturating devices are composed of a discoid part made of a slightly flexible material, having a central countersunk hole to receive the head of the needle that passes through it. This discoid part has, on its front side, appendages adapted to operate on the retention devices as the discoid part is pushed forward by the front end of the piston, when it completes its operative run. The retention devices are constituted by many flexible tongues which rise from the wall of the tube at a slanting angle, pointing forward and inward, and which are set so that they become fitted into a ring-shaped external groove made around the outside of the needle's head, from where they are removed as they are bent by means of the pushing action of the appendages of the obturating discoid part.

2 Claims, 2 Drawing Sheets

DISPOSABLE HYPODERMIC SYRINGE

BACKGROUND OF THE INVENTION

This invention deals with a disposable hypodermic syringe of the type which is rendered unusable after it has been used once, comprising a tube, with its front part narrowed and adapted to receive a hypodermic needle, and a hollow piston, which slides through the inside of the tube. In this front inside part of the tube, there are also obturating devices which are laid across and held in an operative position by the head of the needle. The head of the needle is in turn pressed by a spring which tends to push it towards the inside of the tube, where it is held by interlocking retention devices placed in the front inside part of the tube. There is also a device with irreversible joining retention appliances, which closes the cavity of the piston, and which will work together with other complementary joining devices on the head of the needle when they come into contact once the piston has completed its operative run.

The use of disposable hypodermic syringes which are sold in sterilized and sealed packages of one unit each and which are broken and thrown away after they are used once, is well known.

However, although these syringes are made and sold to be used only once, the truth is that their structural characteristics allow their repeated use without any difficulty from the mechanical point of view, although this gives rise to obvious and very serious problems in the area of health.

These problems have become more acute recently, since the appearance of AIDS, which eventually causes the death of the patient, and for which there is still no known cure or vaccination which will stop it from spreading.

Although there have been attempts to come up with disposable syringes to avoid their repeated use, the only ones which really work are those which, automatically and without any subsequent handling by the user, prevent any further use.

Among all the ones known which are really very few, the most efficient one is the syringe described in Spanish Patent No. 8900179, which belongs to the present invention where, as the piston completes its operative run, it springs a mechanism which automatically introduces the needle into an axial cavity inside the piston, making the removal of the needle from this cavity impossible. This action is complemented in such a way as to prevent the removal of the piston from the inside of the syringe's tube, thus making further use impossible.

However, although the general principle set out in the aforementioned Spanish Patent No. 8900179, is of great effectiveness, the Spanish patent's description of the way in which the syringe is made refers to a syringe made up of a great number of parts, which implies an increase in the costs of manufacture.

SUMMARY OF THE INVENTION

The hypodermic syringe, which is the subject of the present invention, solves the above mentioned problem at a much lower price than the solution disclosed in Spanish Patent No. 8900179.

Basically, the syringe which is the subject of the present invention, is characterized by the fact that the obturating devices already mentioned are composed of a discoid part made of a slightly flexible material, its edge being in contact with the inside wall of the front part of the tube, accomplishing a tight sealing with the latter. The discoid part has a central countersunk hole to receive the head of the needle which passes through it, accomplishing also a tight sealing with the aforementioned conical end. The discoid part has, on its front side, appendages adapted to operate on the interlocking retention devices in the inside front part of the tube as the discoid part is pushed forward by the front part of the piston when its completes its operative run, so that the discoid part, and the needle with it, move slightly forward as they are pushed by the piston. The previously mentioned appendages, in turn, push the retention devices, thereby releasing the needle, which is introduced into the piston's cavity through the spring's action.

According to a further characteristic of the present invention, the interlocking retention appendages in the front part of the tube are made up of a great number of flexible tongues which rise from the wall of the tube at a slanting angle, facing forward and inward, and which are set so that they become fitted into a ring-shaped external groove made around the outside of the needle's head, from where they are removed as they are bent by means of the pushing action of the appendages of the obturating discoid part previously mentioned.

Considering another characteristic of the invention, the closing device of the tube's cavity, which was mentioned earlier, is constituted by a discoidal button, with its edge pressure-fitted into a ring-shaped groove made around 10 the mouth of the piston's cavity. This discoid button has a protuberance in its front part, which constitutes the aforementioned irreversible joining devices, and which has an external stepped protruding edge round it, which will become pressure-fitted into the countersunk hole in the needle's head, from where it is impossible to be extracted, due to the opposing action of the complementary interlocking retention devices, which, in turn, consist of an indented step.

Another feature of the present invention is a set of piston-retaining devices that have been arranged at the mouth of the tube's cavity, which make the total extraction of the piston from the tube impossible.

BRIEF DESCRIPTION OF THE DRAWINGS

The attached drawings show, by way of an example not to be considered as exclusive, a way in which the hypodermic syringe, subject of this invention, can be made.

DETAILED DESCRIPTION

Figure 1:
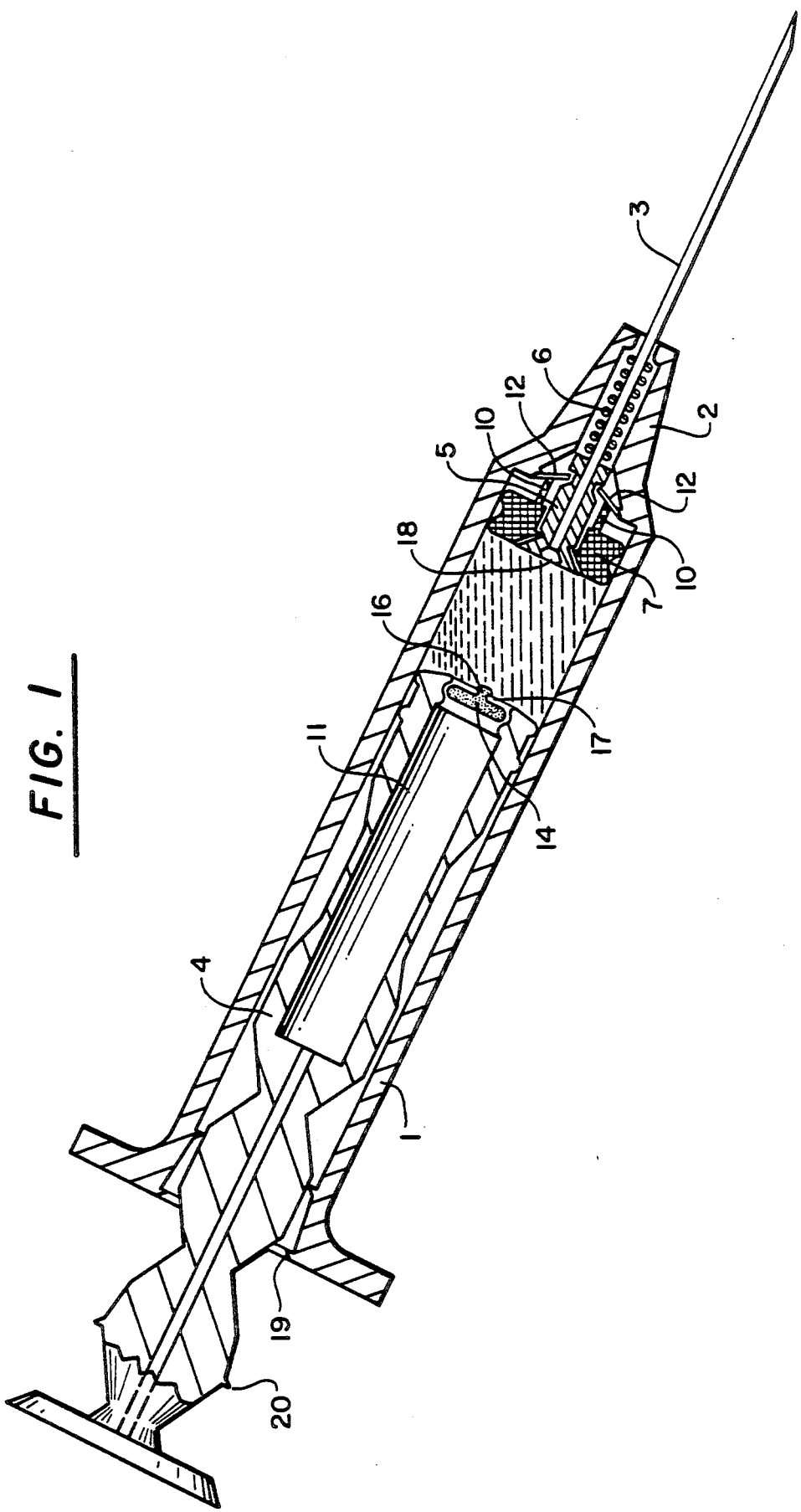
FIG. 1 is a longitudinal cross-sectional view of the syringe, prior to its use.
Figure 2:
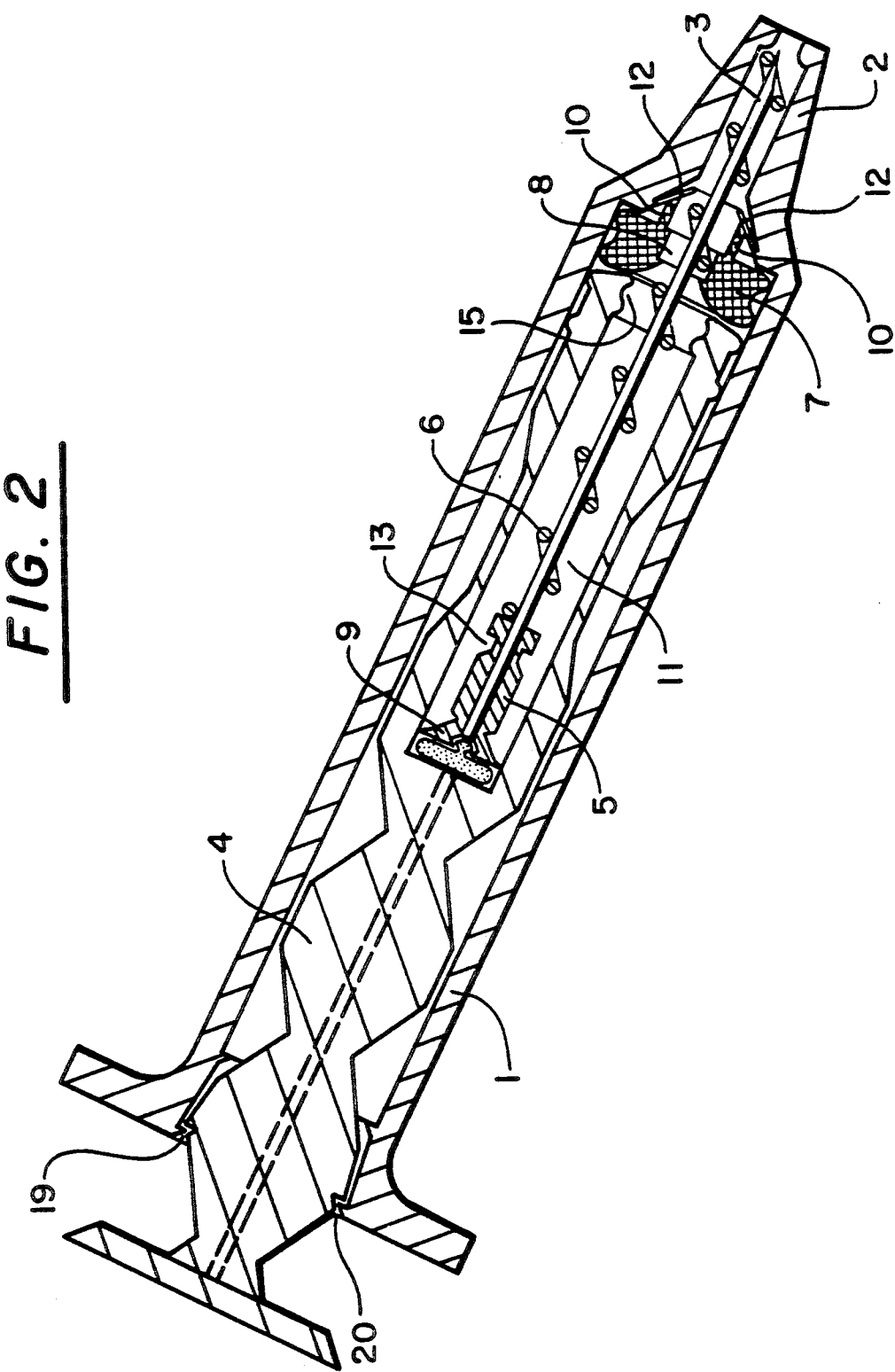
FIG. 2 is a similar view of the one shown in FIG. 1, but once the syringe has been rendered useless.

The accompanying drawings show that the disposable hypodermic syringe, which is the subject of this invention is comprised of a tube 1, with its front part 2 narrowed and adapted to receive a hypodermic needle 3, and a piston 4 capable of sliding longitudinally along the inside of the tube 1.

Obturating devices laid across and held in an operative position by the head 5 of the needle 3 are set in a front inside part of the tube 1.

The head 5 of the needle is pressed by a spring 6, constituted preferably by a helicoidal compression spring, which tends to push it towards the inside of the tube 1, and is held by interlocking retention devices placed in the inside part of the tube 1.

At the front end of the piston 4, there is a closing device of the piston's cavity 11, having irreversible joining devices to fit other complementary joining devices placed at the head 5 of the needle 3.

The aforementioned obturating devices are composed of a discoid part 7 of slightly flexible material, its edge being in contact with the inside wall of the front part of the tube 1, accomplishing a tight sealing with the latter.

The discoid part 7 has a central countersunk hole 8 to receive the head 5 of the needle 3 which passes through it, accomplishing also a tight sealing with the aforementioned conical end 9.

The discoid part 7 also has, on its front side, appendages 10 adapted to operate on the interlocking retention devices in the inside front part of the tube 1, as the discoid part 7 is pushed forward by the front part of the piston 4, when it completes its operative run.

At this stage, the discoid part 7, and the needle 3 with it, move slightly forward as they are pushed by the piston 4. The previously mentioned appendages 10, in turn push the retention devices, thereby releasing the needle 3, which is introduced into the piston's 4 cavity 11 through the action of the spring 6.

The aforementioned interlocking retention devices in the front part of the tube 1 are made up of a great number of flexible tongues 12, which rise from the wall of the tube 1 at a slanting angle, facing forward and inward, and which are set so that they become fitted into a ring-shaped external groove 13 made around the outside of the needle's 3 head 5, from where they are removed as they are bent by means of the pushing action of the appendages 10 of the obturating discoid part 7 previously mentioned.

The aforementioned closing device of the piston's cavity 11 is constituted by a discoid button 14 with its edge pressure-fitted into a ring-shaped groove 15 made around the mouth of the piston's cavity 11.

This discoid button has a protuberance 16, which constitutes the aforementioned irreversible joining devices, and which has an external stepped protruding edge round it 17, which will become pressure-fitted into the countersunk hole 18 in the needle's 3 head 5, from where it is impossible to be extracted due to the opposing action of the complementary interlocking retention devices, which, in turn, consist of an indented step.

A set of piston 4-retaining devices for the piston 4 that have been arranged at the mouth of the tube's 1 cavity, constituted preferentially by joining ribs 19 and 20 make the total extraction of the piston from the tube 1 impossible.

As the nature of the invention, as well as the way of putting it into practice, has been sufficiently described, it is put to record that anything that does not alter, change or modify its main principle may be subject to variations of detail. What is defined in the following claims constitute the invention.

I claim:

1. A disposable hypodermic syringe designed to be used only once, comprising:
   a tubular barrel having a leading end and a trailing end and a longitudinally extending sidewall having a radially inwardly facing internal surface; said tubular barrel further including at said leading end a leading end part which necks down in internal diameter at an internal shoulder and extends longitudinally with a bore having a smaller internal diameter than that of said sidewall; said leading end part having a leading end out through which said bore opens out of said barrel;
   means defining a plurality of flexible tongues arranged in within said barrel in a ring, said tongues having outer ends mounted to said sidewall of said barrel adjacent a trailing end of said leading end part of said barrel, said tongues obliquely projecting radially inwardly and axially towards said leading end of said leading end part from said outer ends thereof, terminating in respective radially inner ends, so as to partially internally obdurate said barrel adjacent said internal shoulder;
   a hypodermic needle having a longitudinal bore, a leading end arranged to be penetrated into a subject, when exposed from said barrel, and a trailing end disposed within said barrel; said needle, between said leading and trailing ends thereof, extending longitudinally within said bore; said hypodermic needle, adjacent said trailing ends thereof having an enlarged head which at said trailing end provides a countersunk opening into said longitudinal bore of said needle and a flaring external shoulder;
   a discoidal part disposed in said barrel and being made of flexible material; said discoidal part having a radially outer portion circumferentially disposed in sliding sealing engagement with said inwardly facing internal surface of said sidewall of said barrel and being arranged, prior to use of said needle, so as to have a longitudinally bore of said discoidal part slidingly receive and circumferentially surround said enlarged head of said needle, with a trailing end of said discoidal part engaged against said flaring external shoulder of said enlarged head of said needle;
   said discoidal part further having on a leading end thereof appendage means which extend longitudinally towards said leading end of said needle and engage said flexible tongues of sites radially intermediate said inner and outer ends of said flexible tongues;
   means defining a spring cavity in said leading end part of said barrel, said spring cavity having a radial shoulder formed therein adjacent where said bore of said leading end part opens out of said barrel;
   a compression coil spring having a leading end engaged against said radial shoulder of said spring cavity, and having a trailing end engaged with said enlarged head of said needle; said compression coil spring being at least partially housed in said spring cavity, and spiralingly surrounding said needle;
   said radially inner ends of said flexible tongues, prior to use of said needle, being axially spaced from said internal shoulder of said leading end part of said barrel;
   said enlarged head of said needle further having a radially outwardly opening circumferentially extending groove in which, prior to use of said needle, said radially inner ends of said flexible tongues are seated, with said compression coil spring thereby held in an axially compressed condition;
   a piston telescopically received in said barrel through said trailing end of said barrel and arranged to be slid axially from an outer position in which a leading end of said piston is substantially spaced from said head of said needle, thereby defining a fluid-receiving cavity within said barrel, and an inner position, in which the leading end of said piston engages said discoidal part and pushes said discoidal part sufficiently towards said leading end of said needle as to cause said appendage means on said discoidal part to flex said flexible tongues towards said internal shoulder sufficiently to unseat said radially inner ends of said flexible tongues from said groove, thereby releasing said spring to recover from its compressed condition, and thus retract said needle into said barrel;

said piston having a cavity extending longitudinally therein and opening centrally of said leading end of said piston, to receive said enlarged head and a longitudinally adjoining intermediate portion of said needle, as needle is retracted into said barrel by recovery of said spring; said spring having sufficient travel while recovering as to sufficiently retract said needle into said barrel that said leading end of said needle no longer emerges from said bore of said lead end part of said barrel.

2. The disposable hypodermic syringe of claim 1, further comprising:

means defining a radially inwardly opening circumferential groove in said piston, within said piston cavity, near said leading end of said piston, this groove, prior to use of said needle, receiving a discoidal button having a central protuberance which is axially aligned with and faces, but is axially spaced from, said countersunk opening into said longitudinal bore of said needle, said discoidal button being so arranged that as said piston is advanced from its outer position to its inner position, said protuberance is forced into said countersunk opening and said discoidal button is dislodged from said radially inwardly opening circumferential groove in said piston, so as to be driven on said enlarged head of said needle, axially further into said cavity of said piston.

* * * * *